United States Patent
Tateno et al.

(10) Patent No.: US 9,731,285 B2
(45) Date of Patent: Aug. 15, 2017

(54) PROCESS FOR PRODUCING OXIDE CATALYSTS

(75) Inventors: Eri Tateno, Tokyo (JP); Masatoshi Kaneta, Tokyo (JP)

(73) Assignee: ASAHI KASEI CHEMICALS CORPORATION, Tokyo (JP)

(*) Notice: Subject to any disclaimer, the term of this patent is extended or adjusted under 35 U.S.C. 154(b) by 1033 days.

(21) Appl. No.: 12/810,493

(22) PCT Filed: Dec. 11, 2008

(86) PCT No.: PCT/JP2008/072563
§ 371 (c)(1),
(2), (4) Date: Jun. 24, 2010

(87) PCT Pub. No.: WO2009/081758
PCT Pub. Date: Jul. 2, 2009

(65) Prior Publication Data
US 2010/0286432 A1 Nov. 11, 2010

(30) Foreign Application Priority Data
Dec. 26, 2007 (JP) .................. 2007-333655

(51) Int. Cl.
| | | |
|---|---|---|
| B01J 21/00 | (2006.01) | |
| B01J 23/00 | (2006.01) | |
| B01J 25/00 | (2006.01) | |
| B01J 29/00 | (2006.01) | |
| B01J 35/02 | (2006.01) | |
| B01J 23/28 | (2006.01) | |
| B01J 23/30 | (2006.01) | |
| B01J 23/34 | (2006.01) | |
| B01J 27/057 | (2006.01) | |
| B01J 37/00 | (2006.01) | |
| B01J 37/08 | (2006.01) | |
| C07C 253/24 | (2006.01) | |

(52) U.S. Cl.
CPC ........... B01J 35/023 (2013.01); B01J 23/002 (2013.01); B01J 23/28 (2013.01); B01J 23/30 (2013.01); B01J 23/34 (2013.01); B01J 27/0576 (2013.01); B01J 37/0045 (2013.01); B01J 37/08 (2013.01); C07C 253/24 (2013.01); B01J 2523/00 (2013.01); Y02P 20/52 (2015.11)

(58) Field of Classification Search
USPC ............... 502/248, 312, 313, 100, 300, 305
See application file for complete search history.

(56) References Cited

U.S. PATENT DOCUMENTS

| | | | |
|---|---|---|---|
| 4,107,085 A | 8/1978 | Sasaki et al. | |
| 4,290,922 A * | 9/1981 | Umemura | ............ B01J 23/8876 502/243 |
| 5,907,052 A | 5/1999 | Hamada et al. | |
| 6,740,769 B1 | 5/2004 | Mizutani et al. | |
| 2004/0076562 A1* | 4/2004 | Manzanec | ............ B01J 19/0093 422/198 |
| 2006/0063951 A1* | 3/2006 | Yunoki | .................. B01J 23/002 562/547 |
| 2006/0235238 A1* | 10/2006 | Komada | .................. B01J 23/28 558/323 |

FOREIGN PATENT DOCUMENTS

| | | |
|---|---|---|
| JP | 52-140490 | 11/1977 |
| JP | 08-141401 | 6/1996 |
| JP | 2001-29788 | 2/2001 |
| JP | 2002-233768 A | 8/2002 |
| JP | 2002-292284 | 10/2002 |
| JP | 2002-301373 | 10/2002 |
| JP | WO-2004/108278 | 7/2006 |
| JP | 2006-248919 | 9/2006 |

OTHER PUBLICATIONS

International Search Report from the Japanese Patent Office for International Application No. PCT/JP2008/072563 (dated Feb. 3, 2009).
International Preliminary Report on Patentability dated Jul. 29, 2010 issued in corresponding International Application No. PCT/JP2008/072563.
Supplementary Search Report dated Apr. 8, 2011 issued in corresponding European patent application.

* cited by examiner

*Primary Examiner* — James McDonough
(74) *Attorney, Agent, or Firm* — Finnegan, Henderson, Farabow, Garrett & Dunner, LLP

(57) ABSTRACT

An object of the present invention is to provide a process for producing an oxide catalyst used in a vapor-phase catalytic oxidation or vapor-phase catalytic ammoxidation reaction of propane or isobutene, which enables a catalyst demonstrating favorable yield to be stably produced. According to the present invention, there is provided a process for producing an oxide catalyst used in a vapor-phase catalytic oxidation or vapor-phase catalytic ammoxidation reaction of propane or isobutene, comprising the steps of: (i) preparing a catalyst raw material mixture containing Mo, V and Nb and satisfying the relationships of $0.1 \leq a \leq 1$ and $0.01 \leq b \leq 1$ when atomic ratios of V and Nb to one atom of Mo are defined as a and b, respectively; (ii) drying the catalyst raw material mixture; and (iii) calcining a particle, in which a content of the particle having a particle diameter of 25 μm or less is 20% by mass or less and a mean particle diameter is from 35 to 70 μm, in an inert gas atmosphere.

9 Claims, No Drawings

PROCESS FOR PRODUCING OXIDE CATALYSTS

TECHNICAL FIELD

The present invention relates to a process for producing oxide catalysts used in a vapor-phase catalytic oxidation or vapor-phase catalytic ammoxidation reaction of propane or isobutane.

BACKGROUND ART

Processes for producing (meth)acrylonitrile by an ammoxidation reaction of propylene or isobutylene as well as processes for producing (meth)acrylic acid by an oxidation reaction of propylene or isobutylene are known in the prior art. More recently, processes for producing (meth)acrylonitrile by a vapor-phase ammoxidation reaction of propane or isobutane and processes for producing (meth)acrylic acid by a vapor-phase catalytic ammoxidation reaction of propane or isobutane are attracting attention as alternatives to such processes using propylene or isobutylene.

Patent document 1 describes a catalyst used in a vapor-phase catalytic oxidation reaction or vapor-phase catalytic ammoxidation reaction of propane or isobutane having a specific reduction ratio and specific surface area. This catalyst having the specific reduction ratio and specific surface area is described as exhibiting suitable activity, having favorable reaction performance (selectivity and yield of target product) and demonstrating little decrease in yield over time.

On the other hand, a fluidized bed reaction is preferable for the reaction form used for vapor-phase catalytic oxidation or vapor-phase catalytic ammoxidation for reasons such as facilitating dissipation of reaction heat enabling the temperature of the catalyst layer to be maintained nearly uniformly, and facilitating removal or addition of catalyst to and from the reactor during the course of operation. A catalyst for which particle diameter has been adjusted to a fixed range is disclosed as being used for the catalyst used in the fluidized bed reaction in order to reduce catalyst loss due to dispersion during the reaction or improve fluidity.

Patent document 2 discloses, as an example that focuses on catalyst fluidity, an example of an ammoxidation reaction that uses propylene or isobutylene for the raw material. In this document, it is disclosed that the content of particles having a particle diameter within a range of from 5 to 150 µm is 95% by mass or more, the content of particles having a particle diameter within a range of from 20 to 30 µm is from 3 to 30% by mass, a high nitrile yield is obtained due to being able to achieve a favorable fluidized state, and that catalyst loss is reduced.

Patent document 3 discloses a vapor-phase oxidation reaction by which a molybdenum compound released from a metal oxide catalyst precipitates in the form of acicular crystals on the surface of a reaction apparatus, wherein as a result of reacting using a catalyst in which the proportion of catalyst particles having a particle diameter of 20 µm or less is 2% by mass or less, the intermingling and solidification of small particles among the acicular crystals decreases, and decreases in the heat transfer coefficient of the heat dissipating coil within the reactor, obstruction of lines, increases in catalyst consumption, and coverage of the inner surface of the reaction apparatus by catalyst particles can be prevented.

In addition, Patent documents 4 and 5 (Japanese Patent Application Laid-open Nos. S52-140490 and 2001-29788) disclose processes for separating dry particles outside a desired particle diameter range by applying dry particles obtained from a spray dryer to a classification procedure, crushing the separated dry particles, and reusing by mixing into a slurry prior to spray drying.

Patent document 1: International Patent Publication WO 2004/108278 pamphlet
Patent document 2: Japanese Patent Application Laid-open No. 2002-233768
Patent document 3: Japanese Patent Application Laid-open No: 2006-248919
Patent document 4: Japanese Patent Application Laid-open No. S52-140490
Patent document 5: Japanese Patent Application Laid-open No. 2001-29788

DISCLOSURE OF THE INVENTION

Problems to be Solved by the Invention

The present inventors produced oxide catalysts adjusted to particle diameters within the ranges described in the previously described Patent documents 2 to 5 in order to industrially carry out a vapor-phase catalytic oxidation reaction or vapor-phase catalytic ammoxidation reaction of propane or isobutane. Whereupon, although effects of improving fluidity in the fluidized bed reactor, preventing contamination within the reaction apparatus and reducing catalyst loss as described in the above documents were observed to a certain extent, all-important catalyst performance was completely unsatisfactory. Even though fluidity may be favorable, if the selectivity and yield of the target product are low, it is not possible to achieve practical application of vapor-phase catalytic oxidation or vapor-phase catalytic ammoxidation.

Therefore, as a result of the present inventors of conducting studies to determine the cause of the low catalyst performance, it was found that a catalyst produced by adjusting the particle size as described above does not satisfy the desired reduction ratio. In addition, as a result of further studies, in the case of an oxide catalyst containing V and Nb in addition to Mo, the presence of a catalyst having a small particle diameter in the production step was determined to affect catalyst performance, and particularly adjustment of the reduction ratio of the catalyst or catalyst precursor to be described later. Although Patent document 1 describes that a catalyst containing Mo, V and Nb is obtained at an expected reduction ratio, this is presumed to be due to difficulty in the occurrence of adjustment unevenness of the reduction ratio since the catalyst was prepared on a comparatively small scale in the calcining step and the like.

Namely, as is described in Patent document 1, although oxide reduction ratio is known to be able to affect catalyst performance, a process for producing a catalyst realizing a desirable reduction ratio has yet to be known in the case of large-volume production by long-term continuous calcining by increasing the scale of the calcining step in particular.

With the foregoing in view, an object of the present invention is to provide a process for producing an oxide catalyst used in a vapor-phase catalytic oxidation or vapor-phase catalytic ammoxidation reaction of propane or isobutane, whereby the catalyst demonstrates favorable yield and can be stably produced.

Means for Solving the Problems

As a result of conducting extensive studies to achieve the above-mentioned object, the present inventors found that a catalyst having superior performance can be produced both efficiently and stably by a process for producing an oxide catalyst, which comprises the steps of: (i) preparing a catalyst raw material mixture containing Mo, V and Nb and satisfying the relationships of 0.1≤a≤1 and 0.01≤b≤1 when atomic ratios of V and Nb to one atom of Mo are defined as a and b, respectively, (ii) drying the catalyst raw material mixture, and (iii) calcining particles, in which a content of the particles having a particle diameter of 25 μm or less is 20% by mass or less and a mean particle diameter is 35 to 70 μm, in an inert gas atmosphere, thereby leading to completion of the present invention.

Namely, the present invention is as follows:

[1] A process for producing an oxide catalyst used in a vapor-phase catalytic oxidation or vapor-phase catalytic ammoxidation reaction of propane or isobutane, comprising the steps of:

(i) preparing a catalyst raw material mixture containing Mo, V and Nb and satisfying the relationships of 0.1≤a≤1 and 0.01≤b≤1 when atomic ratios and Nb to one atom of Mo are defined as a and b, respectively, (ii) drying the catalyst raw material mixture, and (iii) calcining a particle, in which a content of the particle having a particle diameter of 25 μm or less is 20% by mass or less and a mean particle diameter is from 35 to 70 μm, in an inert gas atmosphere.

[2] The process for producing the oxide catalyst according to item [1], wherein the step (iii) is a step of calcining the particle, in which the content of the particle having a particle diameter of 25 μm or less is 8% by mass or less and the mean particle diameter is from 45 to 65 μm, in the inert gas atmosphere.

[3] The process for producing the oxide catalyst according to item [1] or [2], wherein the step (ii) is a step of spray drying the catalyst raw material mixture.

[4] The process for producing the oxide catalyst according to any one of items [1] to [3], further comprising classifying the particle obtained by drying in the step (ii).

[5] The process for producing the oxide catalyst according to item [4], wherein a recovery rate of the particle in the classifying step is 75% by mass or more.

[6] The process for producing the oxide catalyst according to any one of items [1] to [5], wherein the oxide catalyst is supported onto 10 to 80% by mass of silica in terms of $SiO_2$, based on a total weight of oxides of constituent elements of the catalyst and the silica.

[7] The process for producing the oxide catalyst according to any one of items [1] to [6], wherein the step (iii) comprises a performing step of main calcining of pre-stage calcined catalyst precursor particles.

[8] The process for producing the oxide catalyst according to item [7], wherein a temperature range of the main calcination is from 550 to 800° C.

[9] The process for producing the oxide catalyst according to item [7], wherein a temperature range of the pre-stage calcination is from 250 to 400° C. and the temperature range of the main calcination is from 580 to 750° C.

[10] The process for producing the oxide catalyst according to any one of items [7] to [9], wherein a calcining method is a continuous method.

[11] The process for producing the oxide catalyst according to any one of items [7] to [10], wherein the calcination is carried out while rotating a calcining device.

[12] A process for producing an unsaturated acid or an unsaturated nitrile, comprising the step of:

bringing propane or isobutane into contact with an oxide catalyst obtained by the process according to any one of items [1] to [11], so as to carry out a vapor-phase catalytic oxidation or vapor-phase catalytic ammoxidation reaction.

Advantageous Effects of the Invention

According to the present invention, a process can be provided for producing the oxide catalyst used in the vapor-phase catalytic oxidation or vapor-phase catalytic ammoxidation reaction of propane or isobutene, whereby this catalyst demonstrating favorable yield is stably produced.

BEST MODE FOR CARRYING OUT THE INVENTION

The following provides a detailed explanation of the best mode for carrying out the present invention (to be referred to as "present embodiment"). Furthermore, the present invention is not limited to the following present embodiment, but rather can be modified in various ways within the scope of the gist thereof.

In the present embodiment, a process for producing an oxide catalyst used in a vapor-phase catalytic oxidation or vapor-phase catalytic ammoxidation reaction of propane or isobutane comprises the steps of: (i) preparing a catalyst raw material mixture containing Mo, V and Nb and satisfying the relationships of 0.1≤a≤1. and 0.01≤b≤1 when atomic ratios of V and Nb to one atom of Mo are defined as a and b, respectively, (ii) drying the catalyst raw material mixture, and (iii) calcining particles, in which a content of the particles having a particle diameter of 25 μm or less is 20% by mass or less and a mean particle diameter is from 35 to 70 μm, in an inert gas atmosphere. In the present embodiment, prior to the calcining step of step (iii), the particles supplied to calcination are adjusted so that the content of particles having a particle diameter of 25 μm or less is 20% by mass or less and the mean particle diameter is from 35 to 70 μm.

[Step (i)]

Step (i) is a step of preparing a catalyst raw material mixture containing Mo, V and Nb and satisfying the relationships of 0.1≤a≤1 and 0.01≤b≤1 when the atomic ratios of V and Nb to one atom of Mo are defined as a and b, respectively.

The catalyst raw material mixture of the present embodiment contains Mo, V and Nb and satisfies the relationships of 0.1≤a≤1 and 0.01≤b≤1 and preferably relationships of 0.15≤a≤0.9 and 0.02≤b≤0.8 when the atomic ratios of V and Nb to one atom of Mo are defined as a and b, respectively.

There are no particular limitations on the raw materials of the component metals used in step (i) provided the raw materials contain Mo, V and Nb. Examples of Mo raw materials may include molybdenum oxide, ammonium dimolybdenate, ammonium heptamolybdenate, phosphomolybdenic acid and silicomolybdenic acid, and ammonium heptamolybdenate can be used particularly preferably. Examples of V raw materials may include vanadium pentoxide, ammonium metavanadinate and vanadyl sulfate, and ammonium metavanadinate can be used particularly preferably. Examples of Nb raw materials may include at least one type selected from the group consisting of niobic acid, inorganic acid salts of niobium and organic acid salts of niobium, and niobic acid is particularly preferable. Niobic acid is represented by $Nb_2O_5 \cdot nH_2O$, and is also referred to as niobium hydroxide or niobic oxide hydrate. In particular, niobium raw materials may include those containing dicarboxylic acids and niobium compounds, and niobium raw materials in which the molar ratio of dicarboxylic acid to niobium is from 1 to 4 are used preferably. With respect to other elements, telluric acid can be used preferably as a Te raw material in the case of adding Te, and antimony oxides can be preferably used as an Sb raw material in the case of adding Sb.

In step (i), a catalyst raw material mixture is obtained by, for example, preparing a solution by dissolving each of the above raw materials in a solvent such as water followed by mixing the resulting solutions.

The following provides an explanation of this step using the example of a catalyst raw material mixture containing Mo, V, Nb and Sb.

Ammonium heptamolybdenate, ammonium metavanadinate and diantimony trioxide powder are added to water and heated to 80° C. or higher to prepare a mixed solution (A). At this time, in the case the catalyst contains Te, B and Ce, for example, telluric acid, boric acid and cerium nitrate can be added simultaneously.

Next, niobic acid and oxalic acid are heated and stirred in water to prepare a mixed solution (B). The mixed solution (B) is obtained using the method indicated below. Namely, an aqueous solution or aqueous suspension is obtained by adding niobic acid and oxalic acid to water followed by stirring. In the case of suspending, dissolution of niobium compounds can be promoted by adding a small amount of aqueous ammonia or heating. Next, the aqueous solution or aqueous suspension is cooled and filtered to obtain a niobium-containing liquid. Cooling can be conveniently carried out by cooling with ice while filtering can be conveniently carried out by decantation or filtration. The resulting niobium-containing liquid can also be prepared to a preferable ratio of oxalic acid/niobium by suitably adding oxalic acid. The molar ratio of oxalic acid/niobium is preferably from 2 to 5 and more preferably from 2 to 4. Moreover, the mixed liquid (B) may also be prepared by adding hydrogen peroxide to the resulting niobium mixed liquid. At this time, the molar ratio of hydrogen peroxide/niobium is preferably from 0.5 to 20 and more preferably from 1 to 10.

Next, the mixed liquid (A) and the mixed liquid (B) are mixed according to target composition to obtain a raw material mixture. For example, in the case of containing W and Mn in the catalyst, the raw material mixture is obtained by suitably mixing a compound containing W. An example of a compound containing W that is used preferably is ammonium metatungstenate. An example of a compound containing Mn that is used preferably is manganese nitrate. A compound containing W and Mn can be added to the mixed liquid (A) or can be simultaneously added when mixing the mixed liquid (A) and the mixed liquid (B). In the case an oxide catalyst is supported onto a silica support, the raw material mixture can be prepared so as to contain a silica sol, and this case, the silica sol can be suitably added.

Although metal components contained in the catalyst raw material mixture can have various oxidation numbers, from the viewpoint of stable industrial production of catalyst, the metal components are preferably oxidized to the respective maximum oxidation number or state close thereto in the catalyst step (i). Furthermore, during the course of preparation, it is not realistic to investigate the oxidation number of each metal, and although this is not required, a preferable mode can be said to be that in which the catalyst raw material mixture is prepared in a state in which oxidation progresses. Furthermore, the reason why it is preferable to prepare the catalyst raw material mixture in a state in which oxidation progresses is that, since the catalyst is oxidized in this step after which reduction progresses in the subsequent calcining step, it is thought to be easier to obtain a catalyst having a preferable reduction ratio in an industrially stable manner.

Although there are no particular limitations on the method for oxidizing the catalyst raw material mixture so that the metal components thereof reach the maximum oxidation number or oxidation number close thereto, in the case of containing antimony, an example of such a method may include adding hydrogen peroxide to the mixed liquid (A) or a solution containing components of the mixed liquid (A) during the course of mixture. At this time, the molar ratio of $H_2O_2/Sb$ is preferably from 0.01 to 5 and more preferably from 0.05 to 4. In addition, at this time, stirring is preferably continued at from 30 to 70° for 30 minutes to 2 hours. The catalyst raw material mixture obtained in this manner is generally in the form of a slurry although there are cases in which it is in the form of a homogeneous solution.

[Step (ii)]

Step (ii) is a step of drying the catalyst raw material mixture.

In this step, a dry powder is obtained by drying the catalyst raw material mixture obtained in step (i). Drying can be carried out with the known method, and although drying can be carried out by, for example, spray drying or evaporating to dryness, it is preferable to obtain a dry powder in the form of microspheres by spray drying. The atomization in the spray drying method can be carried out by the centrifugal method, two-fluid nozzle method or high-pressure nozzle method. Air heated by steam or an electric heater and the like can be used for the drying heat source. The dryer inlet temperature of the spraying drying apparatus is preferably from 150 to 300° C., and the dryer outlet temperature is preferably from 100 to 160° C.

A catalyst powder or catalyst precursor is prepared such that the content of particles having a particle diameter of 25 μm or less is 20% by mass or less, preferably 15% by mass or less, more preferably 10% by mass or less, even more preferably 5% by mass or less, and still more preferably 2% by mass or less. Here, the term "catalyst precursor" refers to a compound that is formed at an intermediate stage of the calcining step to be described later. For example, that obtained following a pre-stage calcination to be described later is referred to as a catalyst precursor. If the content of particles having a particle diameter of 25 μm or less exceeds 20% by mass, the performance of the resulting catalyst worsens, and the yield of the target product in the fluidized bed reaction apparatus tends to decrease.

Although the reason for deterioration of catalyst performance is unclear, it is probably due to increased susceptibility to uneven calcination of catalyst precursor particles within the calcining device resulting from poor fluidity if the content of particles having a particle diameter of 25 μm or less exceeds 20% by mass. In the case of continuous calcination in particular, since catalyst precursor particles having a small particle diameter end up returning to the calcining device and being exposed to the calcining atmosphere for a longer amount of time that what is desired, the reduction ratio of the catalyst precursor is not suitable during pre-stage calcination described later. Alternatively, since excessive calcining occurs during main calcination, there is the risk of the occurrence of problems such as crystal decomposition. Moreover, since there is also greater susceptibility to the occurrence of adhesion of catalyst precursor particles, deterioration of catalyst performance is also presumed to be the result of heat transfer to the inside becoming poor due to a laminated layer of substances adhered to the walls of the calcining device or contamination by excessively calcined catalyst adhered for a long period of time. For these reasons, in contrast to it being difficult to stably produce a catalyst having a level of performance (with respect to, for example, yield of target product) equal to that of the case of batch calcining in the case of producing a catalyst by continuous calcining even the catalyst composition is the same, according to the production process of the present embodiment, performance can be obtained at a level equal to that in the case of batch calcining.

In the case Mo, Sb or Te and the like are contained in the catalyst, compounds having a low melting point are easily formed during calcination. Since particles having a particle diameter of 25 μm or less have a larger surface ratio than particles having a particle diameter in excess of 25 μm, they are thought to be adhered more easily. If the adhered amount becomes excessively large, an adequate calcining temperature is unable to be obtained for the catalyst layer, and this results in problems such as being unable to secure an adequate production volume. Accordingly, it is preferable that the ratio of particles having a particle diameter of 25 μm or less be low in the stage prior to calcining.

The dry powder or catalyst precursor is prepared to have a mean particle diameter of from 35 to 70 μm, preferably from 40 to 65 μm, more preferably from 42 to 65 μm, still more preferably from 45 to 63 μm, and even more preferably from 45 to 60 μm. If the mean particle diameter is less than 35 μm, fluidity becomes poor, yield of the target product in the fluidized bed reaction decreases, and there is increased dispersion from the fluidized bed reactor, thereby resulting in the risk of a considerable loss of the amount of catalyst. If the mean particle diameter exceeds 70 μm, fluidity becomes poor and contact efficiency with the reaction gas becomes poor, thereby resulting in the risk of a decrease in yield of the target product in the fluidized bed reaction.

Prior to the calcining step to be described later (or main calcination depending on the case), the reduction ratio of the catalyst precursor can be adjusted to a preferable range in the calcining step by adjusting the mean particle diameter of the dry powder or catalyst precursor to be from 35 to 70 μm, and the content of particles having a particle diameter of 25 μm or less to be 20% by mass or less. The present inventors perceive this mechanism to be as described below.

Since the dry powder generally contains ammonium radicals, organic add and inorganic acid, in the case of calcining while allowing an inert gas to flow through the calcining device, catalyst constituent elements are reduced during evaporation and decomposition thereof. Ammonium radicals become ammonia gas when evaporated and reduce catalyst precursor particles from the vapor phase. The reduction ratio of the catalyst precursor varies according to calcining time and calcining temperature particularly during pre-stage calcination to be described later. In the case of a long calcining time or in the case of a high calcining temperature, reduction proceeds easily resulting in a higher reduction ratio. In the case of containing a large number of precursor having a comparatively small particle diameter, if the mean particle diameter typically is less than 35 μm or the content of particles having a particle diameter of 25 μm or less exceeds 20% by mass, the precursor is accompanied by inert gas, numerous small particles rise up together with rotation of the calcining tube or return to the calcining tube, particles are present for which the duration of retention in the calcining tube becomes longer than a desired duration, and it becomes difficult to maintain the reduction ratio within a preferable range. In addition, a large number of small particles are thought to be easily reduced due to having a large surface that contacts ammonia gas. Conversely, since the particles become large when the mean particle diameter exceeds 70 μm, the amount of surface that contacts ammonia gas decreases making it difficult for such particles to be reduced. As a result, it is again difficult to adjust the reduction ratio to a preferable range.

Here, the content of particles having a particle diameter of 25 μm or less is the value obtained by applying 20 g of dry powder or catalyst precursor particles to a sieve while contacting a vibrator therewith (e.g., Panabrator manufactured by National) for 3 minutes using a sieve having a mesh size of 25 μm and diameter of 20 cm, measuring the weight of those particles that passed through the sieve and the weight of those particles remaining on the sieve, and calculating the particle content using the formula indicated below.

(Content of particles of 25 μm or less)=(weight of particles passing through sieve)÷[(weight of particles passing through sieve)+(weight of particles remaining on sieve)]×100

Mean particle diameter is measured by calcining a portion of the dry powder for 1 hour at 400° C. and measuring mean particle diameter from the resulting particles using the Beckman Coulter LS230 laser diffraction/scattering type particle size distribution measuring system.

The reason for measuring the content of particles having a particle diameter of 25 μm or less and mean particle diameter after calcining for 1 hour at 400° C. in air is to prevent the dry powder from melting in water. In other words, the reason for calcining for 1 hour at 400° C. in air is exclusively carried out for the purpose of measurement and is unrelated to the calcining step to be described later. Particle diameter may be considered to remain unchanged before and after calcining. Although there is the possibility of the reduction ratio of a sample calcined in this manner being different from that of other dry powder, since the amount of sample used is generally extremely small, there is no effect on overall catalyst performance regardless of whether or not it is supplied to the calcining step to be described later. Furthermore, the measurement target of mean particle diameter need not always be dry powder, but rather the mean particle diameter of the calcined catalyst precursor may also be measured as necessary.

More specifically, measurement of mean particle diameter is carried out in the following manner in compliance with the manual provided with the Beckman Coulter LS230 laser diffraction/scattering type particle size distribution measuring system. After measuring the background (RunSpeed 60), 0.2 g of particles is weighed in a screw tube of suitable size followed by the addition of 10 cc of water. After capping the screw tube and shaking well, the particles are dispersed in water. Ultrasonic waves of 30 W are applied on the system, and the screw tube is again shaken well. Then the particles dispersed in water are injected into the system with a dropper to a suitable concentration (concentration 10, PIDS 60). Once the concentration display has stabilized, the ultrasonic waves are turned off and measurements are made at 10 second intervals (measurement time: 90 seconds). The median diameter of the measurement results is taken to be the mean particle diameter.

Examples of methods for preparing particles in which the content of particles having a particle diameter of 25 μm or less is 20% by mass or less and the mean particle diameter is from 35 to 70 μm may include methods of adjusting the conditions of atomization and drying, such as the rotating speed of the atomizer, spray drying temperature or feed rate of the raw material mixture, and methods of classifying the dry powder or catalyst precursor. There are no particular limitations on the method of the classification procedure, and an ordinary method can be used, such as that using a centrifugal classifier, air classifier, gravitational classifier, inertial classifier, sieve or cyclone particle separator. If a distinction is made between dry methods and wet methods, a dry classifier can be used preferably. From the viewpoint of increasing the amount of catalyst formed, the recovery rate of dry powder or catalyst precursor particles in the classification procedure is preferably 75% by mass or more and more preferably 80% by mass or more, and conditions are preferably adjusted for that purpose or an apparatus is preferably selected that satisfies such conditions.

There are no particular limitations on the step of adjusting the dry powder or catalyst precursor particles so that the content of particles having a particle diameter of 25 μm or less is 20% by mass or less and the mean particle diameter is from 35 to 70 μm provided that the step is carried out prior to main calcining, and in the case of carrying out pre-stage calcination, can also be carried out after completion of pre-stage calcination. Here, as will be described later, since the pre-stage calcination including calcining in an atmosphere substantially free of oxygen, the catalyst precursor is in a reduced state, and since there is the possibility of the reduction ratio fluctuating from the proper reduction ratio as a result of being oxidized through contact with air, the catalyst precursor is preferably maintained in an atmosphere substantially free of oxygen until main calcination is carried out. Thus, although it is preferable to carry out a classification procedure in an atmosphere substantially free of oxygen in the case of carrying out the classification procedure after pre-stage calcining, since there is the risk of the apparatus and procedure becoming excessively complex as a result of carrying out the classification procedure under such conditions, the step of adjusting the catalyst precursor particles so that the content of particles having a particle diameter of 25 μm or less is 20% by mass or less and the mean particle diameter is from 35 to 70 μm is preferably carried out prior to pre-stage calcining.

[Step (iii)]

In addition to the steps (i) and (ii) as previously described, the production process of the present embodiment further comprises a step (iii) calcining particles in which a content of the particles having a particle diameter of 25 μm or less is 20% by mass or less and a mean particle diameter is from 35 to 70 μm in an inert gas atmosphere.

A rotary kiln or fluidized calcining kiln and the like can be used for the calcining apparatus. If the catalyst precursor particles are calcined while allowed to remain undisturbed, the catalyst precursor particles are not uniformly calcined, which together with causing a decrease in catalyst performance, also causes the formation of splitting, cracking and the like. Thus, in the case of carrying out continuous calcination, a rotary kiln is used preferably.

Although there are no particular limitations on the shape of the calcining device, a tubular furnace enables calcination to be carried out continuously. Although there are no particular limitations on the shape of the calcining tube, a cylindrical calcining tube is preferable. An external heating system is preferable for the heating method, and an electric furnace can be used preferably. Although the size, material and the like of the calcining tube can be suitably selected according to the calcining conditions and production volume, the inner diameter thereof is preferably from 70 to 2000 mm and more preferably from 100 to 1200 mm, and the length is preferably from 200 to 10000 mm and more preferably from 800 to 8000 mm.

In addition, a weir plate having a hole for passage of dry powder or catalyst precursor particles in the center thereof can be provided perpendicular to the flow of catalyst precursor particles in the calcining tube to partition the calcining tube into two or more zones. The installation of a weir plate facilitates the securing of an adequate residence time in the calcining tube. One or a plurality of weir plates may be provided. Metal is preferable for the material of the weir plate, and that made of the same material as that of the calcining tube can be used preferably. The height of the weir plate can be adjusted according to the residence time desired to be secured. For example, in the case of supplying catalyst precursor at 250 g/hr in a rotary kiln having a calcining tube made of SUS and having an inner diameter of 150 mm and length of 1150 mm, the height of the weir plate is preferably from 5 to 50 mm, more preferably from 10 to 40 mm and even more preferably from 13 to 35 mm. There are no particular limitations on the thickness of the weir plate, and is preferably adjusted to match the size of the calcining tube. For example, in the case of a rotary kiln having a calcining tube made of SUS and having an inner diameter of 150 mm and length of 1150 mm, the thickness of the weir plate is preferably from 0.3 to 30 mm and more preferably from 0.5 to 15 mm.

In the calcining step, the calcining device is preferably rotated to prevent splitting and cracking of the catalyst precursor particles as well as to ensure uniform calcination. The rotating speed of the calcining device is preferably from 0.1 to 30 rpm, more preferably from 0.5 to 20 rpm and even more preferably from 1 to 10 rpm.

During calcination of the dry powder or catalyst precursor particles, the heating temperature of the dry powder or catalyst precursor particles is preferably such that heating is started from a temperature lower than 400° C. followed by heating continuously or intermittently to a temperature within a range of from 550 to 800° C.

The calcining step is carried in an inert gas atmosphere. Calcination is preferably carried out while circulating an inert gas substantially free of oxygen such as nitrogen. As was previously described, after obtaining a catalyst demonstrating suitable activity and having favorable reaction performance (in terms of selectivity and yield of the target product), the resulting catalyst preferably has a specific reduction ratio and specific surface area. Since the dry powder is prepared in a state in which oxidation progresses as previously described, at least one constituent element thereof is preferably partially reduced in the calcining step. When calcination is carried out in an inert gas atmosphere, there is the advantage of reduction suitably proceeding due to ammonium radicals, organic acid and inorganic acid contained in the dry powder. In the case the calcining atmosphere is not an inert gas atmosphere, such as if calcination is carried out in air, since the constituent elements are excessively oxidized by the air, it becomes difficult to adjust to a preferable reduction ratio. In addition, if calcination is conversely carried out in a gas capable of reducing the constituent elements, such as in an atmosphere in which excess ammonia is present, the constituent elements are excessively reduced, again making it difficult to adjust to a preferable reduction ratio.

In the above-mentioned catalyst raw material mixture step in particular, in the case of adopting a method involving the addition of hydrogen peroxide to the mixed solution (A), and a raw material mixture is obtained by a step comprising oxidation of molybdenum and vanadium in solution to nearly the maximum oxidation number, the above-mentioned advantage tends to be more conspicuous by carrying out calcination of the dry powder or catalyst precursor particles while circulating an inert gas substantially free of oxygen such as nitrogen. The dry powder or catalyst precursor particles generally contain ammonia radicals, organic acid and inorganic acid in addition to moisture. In the case of calcining while circulating an inert gas substantially free of oxygen, catalyst constituent elements are reduced when they evaporate, decompose and the like. In the case catalyst constituent elements in the dry powder are nearly at the maximum oxidation number, adjustment of the reduction ratio of the catalyst precursor to a desired range only requires that reduction be carried out in the calcining step, thereby making this industrially simple.

In the case of carrying out calcination by batch processing, the supply rate of the inert gas is 50 N liters/hr or more, preferably from 50 to 5000 N liters/hr and more preferably from 50 to 3000 N liters/hr (wherein N liters refers to liters as measured under standard temperature and pressure conditions, namely at 0° C. and 1 atm), based on 1 kg of catalyst precursor particles. In the case of carrying out calcination by continuous processing, the supply rate of the inert gas is 50 N liters or more, preferably from 50 to 5000 N liters and more preferably from 50 to 3000 N liters based on 1 kg of catalyst precursor particles. At this time, although the flows of inert gas and dry powder or catalyst precursor particles may be in the form of counter flow or parallel flow, counter flow is preferable in consideration of gas components generated from the dry powder or catalyst precursor particles and the trace amount of air entering together with the catalyst precursor particles.

Although the calcining step can be carried out in a single stage, it is preferable to carry out pre-stage calcination prior to carrying out main clacination in step (iii) since the reduction ratio tends to be easier to efficiently adjust to the proper range. With respect to the temperature ranges used, the pre-stage clacination is preferably carried out at 250 to 400° C. and the main calcination is preferably carried out at 550 to 800° C. The pre-stage calcination and main calcination may be carried out continuously, or the main calcination may be carried out once the pre-stage calcination has been completed. In addition, the pre-stage calcination and main calcination may each be divided into several stages.

In the case of calcining the catalyst precursor particles at 550 to 800° C., calcination is carried out at a temperature higher than the melting point of the metal components contained in the oxide catalyst and/or catalyst precursor. Consequently, metal components having a low melting point melt during calcination and it becomes easy for the oxide catalyst, catalyst precursor and the like to adhere or melt to the inner walls of the calcining tube and form clumps. This causes poor heat transfer, reduced residence time and unstable particle flow in the case of continuous calcination in particular, thereby making it difficult to stably calcine at a desired temperature. In order to inhibit this adhesion to the inner walls of the calcining tube and the formation of clumps, it is preferable to apply an impact to the calcining tube. Since the shape of the catalyst can be favorably maintained particularly in comparison with the case of directly contacting the catalyst using a method such as mechanically scraping off or breaking up substances adhered to the inner walls of the calcining tube, it is preferable to apply an impact indirectly through the outer wall of the calcining tube.

Since the impact applied to the calcining tube depends on the depth to which catalyst precursor supplied to the calcining tube has accumulated within the calcining tube, the diameter, length, wall thickness and material of the calcining tube, the material, type, shape and location of apparatus used to apply the impact, and the frequency at which the impact is applied, these are preferably suitably set. From the viewpoint of adequately reducing adhesion to the inner walls of the calcining tube, the vibration acceleration is preferably 0.1 m/s$^2$ or more, more preferably 1 m/s$^2$ or more, even more preferably 5 m/s$^2$ or more and particularly preferably 10 m/s$^2$ or more. In addition, from the viewpoints of preventing damage to the calcining tube and not disturbing the flow of particles passing through the calcining tube, the vibration acceleration is preferably 3000 m/s$^2$ or less, more preferably 1000 m/s$^2$ or less, even more preferably 500 m/s$^2$ or less and particularly preferably 300 m/s$^2$ or less.

The "vibration acceleration" of the impact applied to the calcining tube refers to the mean value of values measured at locations corresponding to distances of L/4, 3L/8 and L/2 from the powder inlet of the calcining tube in parallel with the direction of powder flow based on the total length of the calcining tube L. The measurement locations are at the same locations as the location where the impact is applied in the cross-sectional direction of the calcining tube. Measurement of vibration acceleration can be carried out with a vibration meter attached to the calcining tube. An example of a vibration meter that can be used is the MD-220 manufactured by Asahi Kasei Technosystem.

There are no particular limitations on the method used to apply the impact, and an air knocker, hammer or hammering apparatus and the like can be used preferably. There are no particular limitations on the material of the portion of the impacting end that makes direct contact with the calcining tube provided it is a material having adequate heat resistance, and for example, ordinary plastics, metals and the like able to withstand impacts can be used, with metals being used particularly preferably. The metal preferably has a hardness to a degree that does not damage or deform the calcining tube, and that comprised of copper or SUS can be used preferably. There are also no particular limitations on the location where the impact is applied, and although the impact can be applied at a location that is suitable in terms of operation, in order to be able to apply the impact directly to the calcining tube without waste, the impact is preferably applied at a location of the calcining tube that is not covered by the heating oven.

The impact may be applied at a single location or at multiple locations. The impact is preferably applied from a direction other than the direction parallel to the axis of rotation in order to efficiently transmit the vibrations. Although there are no particular limitations on the frequency at which the impact is applied, the impact is preferably steadily applied to the calcining tube since adhesion to the inside of the calcining tube tends to be more favorably reduced. Here, the steady application of impact refers to the application of impacts at a fixed frequency or greater. Impacts are preferably applied at once every 1 second to 1 hour, more preferably once every 1 second to 30 minutes, even more preferably once every 1 second to 5 minutes, and particularly preferably once every 1 second to 1 minute. Impacts are not always required to be applied at the same intervals and may be applied randomly. For example, after applying an impact every 10 seconds, the impact may then be applied twice or more every 10 seconds and then returned to a frequency of being applied once every 10 seconds. The frequency at which impacts are applied is preferably suitably adjusted according to the vibration acceleration, depth of catalyst precursor particles supplied to the calcining tube, diameter, length, wall thickness and material of the calcining tube, and material, type and shape of the apparatus used to apply the impact.

Although there are no particular limitations on the wall thickness of the calcining tube provided it is an adequate thickness to a degree that prevents damage to the calcining tube by the impact, it is preferably 2 mm or more and more preferably 4 mm or more. In addition, from the viewpoint of adequately transmitting the impact to the inside of the calcining tube, the wall thickness is preferably 100 mm or less and more preferably 50 mm or less. There are no particular limitations on the material of the calcining tube provided it has heat resistance and strength that prevents damage to the calcining tube by the impact, and for example, SUS can be used preferably.

In the case of carrying out calcination by dividing into pre-stage calcination and main calcination, the impact is preferably applied during main calcination.

Pre-stage calcination is carried out in the presence of a circulating inert gas at a heating temperature within a range of from 250 to 400° C. and preferably within a range of from 300 to 400° C. Although the heating temperature is preferably maintained at a constant temperature within a range of from 250 to 400° C., the temperature may fluctuate or rise or fall gradually within a range of from 250 to 400° C. The heating temperature retention time is 30 minutes or more and preferably from 3 to 12 hours.

The heating pattern until the pre-stage calcining temperature is reached may increase linearly or may increase while following an upward or downward facing arc.

Although there are no particular limitations on the mean heating rate during heating until the pre-stage clacining temperature is reached, the mean heating rate is preferably from 0.1 to 15° C./min, more preferably from 0.5 to 5° C./min and even more preferably from 1 to 2° C./min.

The main calcination is carried out in the presence of circulating inert gas at a heating temperature of from 550 to 800° C., preferably from 580 to 750° C., more preferably at from 600 to 720° C. and even more preferably at from 620 to 700° C. Although the heating temperature is preferably maintained at a constant temperature within a range of from 620 to 700° C., the temperature may fluctuate or rise or fall gradually within a range of from 620 to 700° C. The duration of the main calcination is from 0.5 to 20 hours and preferably from 1 to 15 hours.

In the case of partitioning the calcining tube with a weir plate, the catalyst precursor particles continuously pass through at least 2 zones, preferably from 2 to 20 zones and more preferably from 4 to 15 zones. Although temperature can be controlled using one or more controllers, in order to obtain a desired calcining temperature pattern as described above, temperature is preferably controlled by installing a heater and controller for each zone partitioned with the weir plates. For example, in the case of installing 7 weir plates so as to divide the length of the portion of the calcining tube that enters the heating oven into 8 equal sections and using a calcining tube partitioned into 8 zones, the temperature of the catalyst precursor particles is preferably controlled to a set temperature by a heater and controller installed for each of the 8 zones so as to obtain the desired calcining temperature pattern as previously described.

Furthermore, an oxidizing component (such as oxygen) or reducing component (such as ammonia) may be added as desired to the calcining atmosphere in the presence of circulating inert gas. As was previously described, since the purpose of calcining the catalyst precursor particles in an inert gas atmosphere is to prevent excessive progression of oxidation or reduction of metal components contained in the catalyst precursor particles during calcination, an oxidizing component or reducing component may be added for adjusting the catalyst reduction ratio to a desired range provided the addition is to a degree that does not have an effect. In actuality, even if calcination is attempted in an inert gas atmosphere, oxygen is unable to be completely removed and oxygen remains on the order of several tens to several hundred ppm. In addition, although ammonia can be generated in the calcining step in the case of containing an ammonium salt in the catalyst raw materials, according to findings obtained by the present inventors, calcination is possible at the expected reduction ratio in either case. From this viewpoint, although the addition of an oxidizing component or reducing component does not constitute a preferred mode of the present embodiment, such components can be said to be able to be added without incident provided they are added to a degree that does not have a substantial effect on the reduction ratio of the calcined catalyst. An amount considered not to have a substantial effect on the reduction ratio of the calcined catalyst in the case of an oxidizing component (such as oxygen) is 0.2 N liters or less, based on 1 kg of the dry powder or catalyst precursor, while that in the case of a reducing component (such as ammonia) is 1.0 N liters or less, based on 1 kg of the dry powder or catalyst precursor.

The heating pattern until the main calcining temperature is reached may increase linearly or may increase while following an upward or downward facing arc.

Although there are no particular limitations on the mean heating rate during heating until the main calcining temperature is reached, the mean heating rate is preferably from 0.1 to 15° C./min, more preferably from 0.5 to 10° C./min and even more preferably from 1 to 8° C./min.

In addition, the mean cooling rate following completion of main calcination is from 0.01 to 1000° C./min, preferably from 0.05 to 100° C./min, more preferably from 0.1 to 50° C./min and even more preferably from 0.5 to 10° C./min. In addition, the cooling temperature is preferably once maintained at a temperature lower than the main calcining temperature. The maintained temperature is 10° C. lower, preferably 50° C. lower and more preferably 100° C. lower than the main calcining temperature. The time during which temperature is maintained is 0.5 hours or more, preferably 1 hour or more, more preferably 3 hours or more and particularly preferably 10 hours or more.

Since the reduction ratio of the catalyst precursor after the pre-stage calcination has an effect on the activity, yield and catalyst life of the oxide catalyst, the reduction ratio is preferably adjusted to a preferable value by adjusting calcining conditions. The reduction ratio of the catalyst precursor is represented by the following formula (1):

$$\text{reduction ratio (\%)} = ((n_0 - n)/n_0) \times 100 \tag{1}$$

(wherein n represents the number of oxygen atoms that satisfy the atomic numbers of constituent elements other than oxygen in the catalyst precursor, and $n_0$ represents the number of oxygen atoms required when each constituent element of the catalyst precursor other than oxygen has their respective maximum oxidation number). The reduction ratio of the catalyst precursor is preferably from 8 to 12%, more preferably from 9 to 11% and even more preferably from 9.5 to 10.5%.

In addition, as long as the reduction ratio is within the desired range, an oxidizing component or reducing component may also be added to the calcining atmosphere. Typically, the amount of organic components such as oxalic acid contained in the dry powder, the amount of ammonium radicals originating from the ammonium salt of the raw materials, the heating rate, temperature and time at the start of calcining and the amount of inert gas and the like have an effect on the reduction ratio of the catalyst precursor. In order to make the reduction ratio of the catalyst precursor from 8 to 12%, heating is started from a temperature lower than 400° C. during calcination, oxalic acid, ammonium radicals and the like in the catalyst precursor particles are decomposed, and the generation of gas is nearly terminated.

In determining the reduction ratio, the value of $(n_0-n)$ in the above-mentioned formula (1) is obtained by redox titration of the sample with $KMnO_4$. An example of a titration method is indicated below.

About 200 mg of sample are accurately weighed into a beaker. Moreover, an excess of a known concentration of aqueous $KMnO_4$ solution is then added. After adding 150 mL of purified water and 2 mL of 1:1 sulfuric acid (namely, aqueous sulfuric acid solution obtained by mixing concentrated sulfuric acid and purified water at a volume ratio of 1/1), the beaker was covered with a watch glass and stirred for 1 hour in a hot water bath at 70±2° C. to oxidize the sample. At this time, since $KMnO_4$ is present in excess and unreacted $KMnO_4$ is present in the liquid, the color of the liquid is confirmed to be violet. Following completion of oxidation, the liquid is filtered with filter paper and the entire volume of filtrate is recovered. An excess amount of a known concentration of aqueous sodium oxalate solution is added based on the $KMnO_4$ present in the filtrate, and the filtrate is heated and stirred so that the liquid temperature reaches 70° C. After confirming that the liquid is colorless and clear, 2 mL of 1:1 sulfuric acid are added. Stirring is continued while maintaining the liquid temperature at 70±2° C. and then titrated with a known concentration of aqueous $KMnO_4$ solution. The endpoint of the titration is taken to be the point at which a slight pink color attributable to $KMnO_4$ persists for about 30 seconds. The amount of $KMnO_4$ consumed by oxidation of the sample is then determined from total amount of $KMnO_4$ and the total amount of $Na_2C_2O_4$. The value of $(n_0-n)$ is then calculated from this value and reduction ratio is determined on the basis thereof.

In addition, besides the measurement method described above, the reduction ratio of the catalyst precursor prior to completion of calcining or that of the catalyst precursor following completion of calcining can also be measured in the manner indicated below.

The sample is heated to a temperature higher than the calcining temperature at which the catalyst precursor or catalyst is calcined under conditions at which constituent elements of the sample do not volatilize or escape, the sample is completely oxidized by oxygen, and the increase in weight (amount of oxygen bound) is determined followed by determining the value of $(n_0-n)$ there from and finally determining the reduction ratio on the basis thereof.

[Oxide Catalyst]

A preferable example of an oxide catalyst according to the present embodiment is represented by the following compositional formula (2):

$$Mo_1V_aNb_bX_cY_dO_n \quad (2)$$

(wherein component X represents at least one type of element selected from the group consisting of Te and Sb; Y represents at least one type of element selected from the group consisting of Mn, W, B, Ti, Al, Ta, alkaline metals and alkaline earth metals; a, b, c, d and n represent the atomic ratios to 1 atom of molybdenum (Mo) of vanadium (V), niobium (Nb), element X, element Y and oxygen (O) and satisfy the relationships of $0.1 \leq a \leq 1$, $0.01 \leq b \leq 1$, $0.01 \leq c \leq 1$ and $0 \leq d \leq 1$; and n represents the number of oxygen atoms determined by the atomic number of constituent elements other than oxygen).

The atomic ratios a, b, c and d based on 1 atom of Mo are preferably $0.1 \leq a \leq 1$, $0.01 \leq b \leq 1$, $0.01 \leq c \leq 1$ and $0 \leq d \leq 1$, more preferably $0.1 \leq a \leq 0.5$, $0.01 \leq b \leq 0.5$, $0.1 \leq c \leq 0.5$ and $0.0001 \leq d \leq 0.5$, and even more preferably $0.2 \leq a \leq 0.3$, $0.05 \leq b \leq 0.2$, $0.2 \leq c \leq 0.3$ and $0.0002 \leq d \leq 0.4$, respectively.

Since adequate strength is required in the case of using the catalyst in a fluidized bed, the oxide catalyst is preferably supported onto a silica support. The oxide catalyst is supported onto silica preferably at 10 to 80% by mass, more preferably at 20 to 60% by mass and even more preferably at 30 to 55% by mass in terms of $SiO_2$ based on the total weight of the oxides of constituent elements of the catalyst and the silica. From the viewpoints of strength, prevention of powdering, ease of stable operation when using the catalyst and decreasing replenishment of lost catalyst, the amount of silica supported with the oxide catalyst is preferably 10% by mass or more based on the total weight of the oxides of the constituent elements of the catalyst and the silica, and from the viewpoint of achieving adequate catalyst activity, is preferably 80% by mass or less based on the total weight of the oxides of the constituent elements of the catalyst and the silica. In the case of using the catalyst in a fluidized bed in particular, if the amount of silica is 80% by mass or less, the specific gravity of the catalyst supported on the silica is suitable thereby facilitating the creation of a favorable fluid state.

[Production of Unsaturated Acid and Unsaturated Nitrile]

Propane or isobutane can be reacted in the vapor phase with molecular oxygen (vapor-phase catalytic oxidation reaction) using the oxide catalyst obtained according to the production process of the present embodiment to produce the corresponding unsaturated carboxylic acid (acrylic acid or methacrylic acid). In addition, propane or isobutane can also be reacted in the vapor phase with ammonia and molecular oxygen (vapor-phase catalytic ammoxidation reaction) using the catalyst to produce the corresponding unsaturated nitrile (acrylonitrile or methacrylonitrile).

The supplied raw materials of the propane or isobutane and ammonia are not required to be of high purity, and industrial grade gases can be used. Air, pure oxygen or air enriched with pure oxygen can be used for the supplied oxygen source. Moreover, helium, neon, argon, carbon dioxide gas, water vapor or nitrogen and the like may be supplied as a dilution gas.

In the case of an ammoxidation reaction, the molar ratio of ammonia to propane or isobutane supplied to the reaction system is from 0.3 to 1.5 and preferably from 0.8 to 1.2. In the case of either an oxidation reaction or ammoxidation reaction, the molar ratio of molecular oxygen to propane or isobutane supplied to the reaction system is from 0.1 to 6 and preferably from 0.1 to 4.

In addition, in the case of either an oxidation reaction or ammoxidation reaction, the reaction pressure is from 0.5 to 5 atm and preferably from 1 to 3 atm, the reaction temperature is from 350 to 500° C. and preferably from 380 to 470° C., and the contact time is from 0.1 to 10 (sec·g/cc) and preferably from 0.5 to 5 (sec·g/cc).

Contact time is defined with the following formula in the present embodiment:

contact time (sec·g/cc)=$(W/F) \times 273/(273+T) \times P$ wherein

W represents catalyst weight (g);

F represents raw material mixed gas flow rate (Ncc/sec) in the standard state (0° C., 1 atm);

T represents reaction temperature (° C.); and

P represents reaction pressure (atm).

Although the conventional system such as a fixed bed, fluidized bed or movable bed can be employed for the vapor-phase catalytic oxidation reaction and the vapor-phase catalytic ammoxidation reaction, for reasons such as facilitating release of reaction heat, being able to maintain the temperature of the catalyst layer nearly constant and enabling catalyst to be added or removed to and from the reactor, a fluidized bed reaction is preferable.

EXAMPLES

Although the following provides a detailed explanation of the present embodiment based on examples and comparative examples thereof, the present embodiment is not limited by these examples.

In the examples and comparative examples, the propane conversion and acrylonitrile yield were respectively defined as indicated below:

Propane conversion (Pn conversion) (%)=(number of moles of propane reacted)/(number of moles of propane supplied)×100

Acrylonitrile yield (AN yield) (%)=(number of moles of acrylonitrile formed)/(number of moles of propane supplied)×100

(Preparation of Niobium Raw Material Liquid)

A niobium raw material liquid was prepared in the following manner. 76.33 kg of niobic acid containing 80.2% by mass as $Nb_2O_5$ and 29.02 g of oxalic acid dihydrate ($H_2C_2O_4.2H_2O$) were mixed into 500 kg of water. The molar ratio of the charged oxalic acid/niobium was 5.0, and the concentration of the charged niobium was 0.532 (mol Nb/kg liquid).

An aqueous solution in which a niobium compound was dissolved was obtained by heating and stirring this liquid for 1 hour at 95° C. After allowing this aqueous solution to stand undisturbed and cooling with an ice, a solid was filtered out by suction filtration to obtain a homogeneous niobium compound aqueous solution. The same procedure was then repeated several times, and the resulting niobium compound aqueous solutions were combined for use as a niobium raw material liquid. The molar ratio of oxalic acid/niobium of this niobium raw material liquid as determined by the analysis described below was 2.60.

10 g of this niobium raw material liquid was accurately weighed into a crucible and after drying overnight at 95° C., the dried product was heat-treated for 1 hour at 600° C. to obtain 0.7868 g of $Nb_2O_5$. On the basis of this result, the niobium concentration was 0.5920 (mol Nb/kg liquid).

3 g of this niobium raw material liquid was accurately weighed into a 300 mL glass beaker followed by the addition of 200 mL of hot water at 80° C. and the addition of 10 mL of 1:1 sulfuric acid. The resulting solution was titrated while stirring using ¼ N $KMnO_4$ while maintaining the liquid temperature at 70° C. on a hot stirrer. The point at which a slight pink color attributable to $KMnO_4$ persists for about 30 seconds or more was defined as the endpoint of the titration. As a result of calculating on the basis of the titrated amount of $KMnO_4$ according to the following formula, the concentration of oxalic acid was determined to be 1.54 (mol oxalic acid/kg):

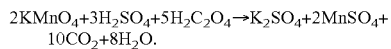

$2KMnO_4+3H_2SO_4+5H_2C_2O_4 \rightarrow K_2SO_4+2MnSO_4+10CO_2+8H_2O$.

The resulting niobium raw material liquid was used as a niobium raw material liquid in the production of an oxide catalyst as described below.

Example 1

A catalyst represented by the compositional formula $Mo_1V_{0.24}Nb_{0.092}Sb_{0.26}O_n$/44 wt %-$SiO_2$ was produced in the manner described below.

(Preparation of Raw Material Mixture)

3.69 kg of ammonium heptamolybdenate [$(NH_4)_6Mo_7O_{24}.4H_2O$], 0.58 kg of ammonium metavanadinate [$NH_4VO_3$] and 0.79 kg of diantimony trioxide [$Sb_2O_3$] were added to 18.07 kg of water followed by heating for 2.5 hours at 90° C. while stirring to obtain aqueous mixed liquid A-1.

0.43 kg of hydrogen peroxide containing 30% by mass as $H_2O_2$ was added to 3.23 kg of the above-mentioned niobium raw material liquid. The liquid was stirred and mixed while maintaining the liquid temperature at about 20° C. to obtain aqueous liquid B-1.

After cooling the resulting aqueous mixed liquid A-1 to 70° C., 6.95 kg of silica sol containing 30.4% by mass as $SiO_2$ was added. Next, 0.92 kg of hydrogen peroxide containing 30% by mass as $H_2O_2$ was added followed by stirring and mixing for 1 hour at 50° C. Next, aqueous liquid B-1 was added. Moreover, a liquid in which 1.41 kg of fumed silica was dispersed in 19.7 kg of water was added to obtain a raw material mixture.

Furthermore, the step of preparing the raw material mixture was repeated 10 times to prepare a total of about 80 kg of raw material mixture in order to continuously carry out the dry powder preparing step and calcining step described below.

(Preparation of Dry Powder)

The resulting raw material mixture was supplied to a centrifugal spray dryer and dried to obtain a dry powder in the form of microspheres. The inlet temperature of the dryer was 210° C. and the outlet temperature was 120° C.

(Classification Procedure)

The resulting dry powder was applied to a classifier and adjusted to the desired fine content and particle diameter. The Turbo Classifier TC-25M manufactured by Nisshin Engineering was used for the classifier. The dry powder was supplied to the classifier at a feed rate of 40 kg/hr, at an air flow rate of 7 m³/min and rotor speed of 1250 rpm. Following classification, the content of the resulting dry powder particles having a particle diameter of 25 µm or less was 1.8% by mass and the mean particle diameter was 55 µm. The mean particle diameter was measured with the Beckman Coulter LS230.

(Calcination)

Seven weir plates having a height of 35 mm were installed in a calcining tube made of SUS and having an inner diameter of 200 mm and length of 1500 mm so as to divide the length of the heating oven portion into 8 equal sections. Continuous pre-stage calcination was carried out by passing the dry powder obtained by the classification procedure through this calcining tube at the rate of 550 g/hr while rotating the calcining tube at 5 rpm, and setting the temperature of the heating oven so that the temperature profile included heating to 360° C. over the course of about 6 hours followed by holding for 2 hours at 360° C. while circulating nitrogen gas at the rate of 8.2 N liters/min. The reduction ratio of the catalyst precursor at this time was 10.23%. Main calcination was then carried out continuously by passing the catalyst precursor through a different calcining tube made of SUS and having an inner diameter of 200 mm and length of 1800 mm installed with seven weir plates having a thickness of 35 mm so as to divide the heating oven portion into 8 equal sections at the rate of 400 g/hr, and setting the temperature of the heating oven so that the temperature profile included heating to 650° C. at the rate of 2° C./min, calcination for 2 hours at 650° C. and then cooling at the rate of 1° C./min while circulating nitrogen gas at the rate of 8.0 N liters/min. During main calcination, a single impact was applied to the powder entry side of the calcining tube (portion not covered by the heating oven) every 15 seconds from a height of 40 mm from the upper portion of the clacining tube in a direction perpendicular to the axis of rotation with a hammering apparatus installed with a hammer having an impacting end made of SUS and weighing 3 kg. During main calcination, there was little adhesion to the inside of the calcining tube, there was no decrease in temperature of the catalyst layer, and discharge remained stable. Measurement of the vibration acceleration with a vibration meter (MD-220 manufactured by Asahi Kasei Technosystem) yielded a value of 51 m/s$^2$.

(Evaluation of Catalyst Performance)

45 g of oxide catalyst was packed into a Vycor glass fluidized bed reactor having an inner diameter of 25 mm, and a mixed gas of propane, ammonia, oxygen and helium at a molar ratio of 1:1:3.0:13, respectively, was passed through at a reaction temperature of 440° C. under a normal pressure and at a contact time of 3.0 (sec·g/cc). As a result of evaluating the performance of the catalyst, the propane conversion was 89% and the acrylonitrile yield was 52.5%.

Example 2

An oxide catalyst was obtained according to the same method as Example 1 with the exception of setting the rotor speed for supplying to the classifier to 1400 rpm. The content of dry powder particles following classification having a particle diameter of 25 μm or less was 4.1% by mass and the mean particle diameter was 52 μm. In addition, the reduction ratio of the catalyst precursor was 9.98%. When the performance of the oxide catalyst in an ammoxidation reaction was evaluated in the same manner as Example 1, the propane conversion was 88.2% and the acrylonitrile yield was 51.8%.

Example 3

An oxide catalyst was obtained according to the same method as Example 1 with the exception of setting the rotor speed for supplying to the classifier to 1500 rpm. The content of dry powder particles following classification having a particle diameter of 25 μm or less was 6.0% by mass and the mean particle diameter was 51 μm. In addition, the reduction ratio of the catalyst precursor was 10.10%. When the performance of the oxide catalyst in an ammoxidation reaction was evaluated in the same manner as Example 1, the propane conversion was 87.9% and the acrylonitrile yield was 51.0%.

Example 4

A catalyst represented by the compositional formula Mo$_1$V$_{0.24}$Nb$_{0.092}$Sb$_{0.26}$O$_n$/44 wt %-SiO$_2$ was produced in the manner described below.

(Preparation of Raw Material Mixture)

0.93 kg of ammonium heptamolybdenate [(NH$_4$)$_6$Mo$_7$O$_{24}$·4H$_2$O], 0.15 kg of ammonium metavanadinate [NH$_4$VO$_3$] and 0.20 kg of diantimony trioxide [Sb$_2$O$_3$] were added to 4.52 kg of water followed by heating for 2.5 hours at 90° C. while stirring to obtain aqueous mixed liquid A-1.

0.11 kg of hydrogen peroxide containing 30% by mass as H$_2$O$_2$ was added to 0.81 kg of the above-mentioned niobium raw material liquid. The liquid was stirred and mixed while maintaining the liquid temperature at about 20° C. to obtain aqueous liquid B-1.

After cooling the resulting aqueous mixed liquid A-1 to 70° C., 1.74 kg of silica sol containing 30.4% by mass as SiO$_2$ was added. Next, 0.23 kg of hydrogen peroxide containing 30% by mass as H$_2$O$_2$ was added followed by stirring and mixing for 1 hour at 50° C. Next, aqueous liquid B-1 was added. Moreover, a liquid in which 0.35 kg of fumed silica was dispersed in 4.93 kg of water was added to obtain a raw material mixture.

(Preparation of Dry Powder)

The resulting raw material mixture was supplied to a centrifugal spray dryer and dried to obtain a dry powder in the form of microspheres. The inlet temperature of the dryer was 210° C. and the outlet temperature was 120° C.

(Classification Procedure)

Classification was carried out by applying 200 g of the resulting raw material mixture to a sieve while contacting with a vibrator for 2 minutes using a sieve having a mesh size of 25 μm and diameter of 20 cm. Following classification, the content of the resulting dry powder particles having a particle diameter of 25 μm or less was 0.2% by mass and the mean particle diameter was 56 μm. The mean particle diameter was measured with the Beckman Coulter LS230.

(Calcination)

100 g of the dry powder particles obtained by the classification procedure was packed into a glass calcining tube having a diameter of 50 mm followed by heating to 360° C. over the course of about 6 hours followed by holding for 2 hours at 360° C. while circulating nitrogen gas at the rate of 0.25 N liters/min and rotating the calcining tube. The reduction ratio at this time was 9.93%. Subsequently, the temperature was raised to 650° C. over the course of 2 hours followed by calcining for 2 hours at 650° C. to obtain a catalyst. When the performance of the oxide catalyst in an ammoxidation reaction was evaluated in the same manner as Example 1, the propane conversion was 88.8% and the acrylonitrile yield was 52.8%.

Example 5

An oxide catalyst was obtained using the same method as Example 1 with the exception of applying a single impact once every 15 seconds from a height of 35 mm from the upper portion of the calcining tube in a direction perpendicular to the axis of rotation with a hammering apparatus installed with a hammer having an impacting end made of SUS and weighing 2 kg. Measurement of the vibration acceleration with a vibration meter (MD-220 manufactured by Asahi Kasei Technosystem) yielded a value of 14 m/s$^2$. When the performance of the oxide catalyst in an ammoxidation reaction was evaluated in the same manner as Example 1, the propane conversion was 88.3% and the acrylonitrile yield was 52.1%.

Example 6

An oxide catalyst was obtained using the same method as Example 1 with the exception of applying a single impact once every 15 seconds from a height of 50 mm from the upper portion of the calcining tube in a direction perpendicular to the axis of rotation with a hammering apparatus installed with a hammer having an impacting end made of SUS and weighing 13 kg. Measurement of the vibration acceleration with a vibration meter (MD-220 manufactured by Asahi Kasei Technosystem) yielded a value of 210 m/s$^2$.

When the performance of the oxide catalyst in an ammoxidation reaction was evaluated in the same manner as Example 1, the propane conversion was 88.4% and the acrylonitrile yield was 52.4%.

Example 7

After obtaining a dry powder using the same method as Example 1, continuous pre-stage calcination was carried out using the same method as Example 1 but without carrying out a classification procedure.

A classification procedure was carried out by applying 200 g of the catalyst precursor particles obtained from pre-stage calcination to a sieve while contacting with a vibrator for 2 minutes using a sieve having a mesh size of 25 μm and diameter of 20 cm. Following classification, the content of the resulting catalyst precursor particles having a particle diameter of 25 μm or less was 0.4% by mass and the mean particle diameter was 54 μm. The mean particle diameter was measured with the Beckman Coulter LS230. The reduction ratio of the catalyst precursor at this time was 10.18%.

90 g of the catalyst precursor particles obtained by the classification procedure was packed into a glass calcining tube having a diameter of 50 mm followed by raising the temperature to 650° C. in 2 hours while circulating nitrogen gas at 0.30 N liters/min and rotating the calcining tube followed by calcining for 2 hours at 650° C. to obtain a catalyst. When the performance of the oxide catalyst in an ammoxidation reaction was evaluated in the same manner as Example 1, the propane conversion was 88.5% and the acrylonitrile yield was 51.9%.

Comparative Example 1

An oxide catalyst was obtained according to the same method as Example 1 with the exception of not carrying out a classification procedure after spray drying. The content of dry powder particles having a particle diameter of 25 μm or less was 25% by mass and the mean particle diameter was 34 μm. The reduction ratio of the catalyst precursor at this time was 10.21%. In addition, the reduction ratio of particles having a particle diameter of 25 μm or less was 10.54%, while the reduction ratio of particles having a particle diameter of 25 μm or more was 10.10%. When the performance of the oxide catalyst in an ammoxidation reaction was evaluated in the same manner as Example 1, the propane conversion was 86% and the acrylonitrile yield was 47.5%.

Comparative Example 2

An oxide catalyst was obtained according to the same method as Example 1 with the exception of setting the rotating speed of the classifier to 3000 rpm. The content of dry powder particles having a particle diameter of 25 μm or less was 22% by mass and the mean particle diameter was 46 μm. The reduction ratio of the catalyst precursor at this time was 10.15%. In addition, the reduction ratio of particles having a particle diameter of 25 μm or more was 10.11%, while the reduction ratio of particles having a particle diameter of 25 μm or less was 10.30%. When the performance of the oxide catalyst in an ammoxidation reaction was evaluated in the same manner as Example 1, the propane conversion was 86.8% and the acrylonitrile yield was 49.5%.

Comparative Example 3

An oxide catalyst was obtained according to the same method as Example 1 with the exception of setting the rotating speed of the classifier to 2500 rpm. The content of dry powder particles having a particle diameter of 25 μm or less was 18% by mass and the mean particle diameter was 34 μm. The reduction ratio of the catalyst precursor at this time was 10.0%. In addition, the reduction ratio of particles having a particle diameter of 25 μm or more was 9.93%, while the reduction ratio of particles having a particle diameter of 25 μm or less was 10.32%. When the performance of the oxide catalyst in an ammoxidation reaction was evaluated in the same manner as Example 1, the propane conversion was 85.0% and the acrylonitrile yield was 48.8%.

Comparative Example 4

An oxide catalyst was obtained according to the same method as Example 1 with the exception of carrying out the classification procedure with a sieve having a mesh size of 53 μm. The content of dry powder particles having a particle diameter of 25 μm or less following classification was 0% by mass and the mean particle diameter was 71 μm. The reduction ratio of the catalyst precursor at this time was 10.08%. When the performance of the oxide catalyst in an ammoxidation reaction was evaluated in the same manner as Example 1, the propane conversion was 87.1% and the acrylonitrile yield was 49.4%.

Comparative Example 5

An oxide catalyst was obtained according to the same method as Example 1 with the exception of not classifying the catalyst precursor particles but rather classifying the catalyst following main calcination under the same conditions as Example 1. The content of catalyst particles having a particle diameter of 25 μm or less following classification was 2% by mass and the mean particle diameter was 53 μm. The reduction ratio of the catalyst precursor at this time was 10.19%. When the performance of the oxide catalyst in an ammoxidation reaction was evaluated in the same manner as Example 1, the propane conversion was 87.6% and the acrylonitrile yield was 49.9%.

Comparative Example 6

An oxide catalyst was obtained according to the same method as Example 1 with the exception of carrying out the calcining step in the presence of circulating air. The reduction ratio of the catalyst precursor at this time was 4.2%. When the performance of the oxide catalyst in an ammoxidation reaction was evaluated in the same manner as Example 1, the propane conversion was 38.7% and the acrylonitrile yield was 6.5%.

Example 8

A catalyst represented by the compositional formula $Mo_1V_{0.24}Nb_{0.092}Sb_{0.26}W_{0.025}O_n$/44 wt %-$SiO_2$ was produced in the manner described below.
(Preparation of Raw Material Mixture)
3.59 kg of ammonium heptamolybdenate [$(NH_4)_6Mo_7O_{24}\cdot 4H_2O$], 0.57 kg of ammonium metavanadinate [$NH_4VO_3$] and 0.77 kg of diantimony trioxide [$Sb_2O_3$] were added to 17.6 kg of water followed by heating for 2.5 hours at 90° C. while stirring to obtain aqueous mixed liquid A-1.

0.42 kg of hydrogen peroxide containing 30% by mass as $H_2O_2$ was added to 3.14 kg of the above-mentioned niobium raw material liquid. The liquid was stirred and mixed while maintaining the liquid temperature at about 20° C. to obtain aqueous liquid B-1.

After cooling the resulting aqueous mixed liquid A-1 to 70° C., 6.95 kg of silica sol containing 30.4% by mass as $SiO_2$ was added. Next, 0.89 kg of hydrogen peroxide containing 30% by mass as $H_2O_2$ was added followed by stirring and mixing for 1 hour at 50° C. Next, aqueous liquid B-1 was added. 0.23 kg of ammonium metatungstenate containing 50.2% by mass as $WO_3$ was then added followed by further adding a liquid in which 1.41 kg of fumed silica was dispersed in 19.71 kg of water to obtain a raw material mixture. The step of preparing the raw material mixture was repeated 10 times to prepare a total of about 80 kg of raw material mixture in order to continuously carry out the dry powder preparing step and calcining step.

(Preparation of Dry Powder)

A dry powder was obtained by carrying out spray drying in the same manner as Example 1.

(Classification Procedure)

Classification was carried out in the same manner as Example 1. The content of the dry powder particles having a particle diameter of 25 μm or less following classification was 1.7% by mass and the mean particle diameter was 52 μm.

(Calcination)

Calcination was carried out in the same manner as Example 1 to obtain an oxide catalyst. The reduction ratio of the catalyst precursor at this time was 10.19%.

(Evaluation of Catalyst Performance)

When the performance of the oxide catalyst in an ammoxidation reaction was evaluated in the same manner as Example 1, the propane conversion was 88.8% and the acrylonitrile yield was 53.0%.

Example 9

A catalyst represented by the compositional formula $Mo_1V_{0.24}Nb_{0.092}Sb_{0.26}W_{0.04}Ce_{0.008}O_n/44$ wt %-$SiO_2$ was produced in the manner described below.

(Preparation of Raw Material Mixture)

3.52 kg of ammonium heptamolybdenate [$(NH_4)_6Mo_7O_{24}.4H_2O$], 0.56 kg of ammonium metavanadinate [$NH_4VO_3$], 0.75 kg of diantimony trioxide [$Sb_2O_3$] and 0.07 kg of cerium nitrate [$Ce(NO_3)_3.6H_2O$] were added to 17.22 kg of water followed by heating for 2.5 hours at 90° C. while stirring to obtain aqueous mixed liquid A-1.

0.41 kg of hydrogen peroxide containing 30% by mass as $H_2O_2$ was added to 3.07 kg of the above-mentioned niobium raw material liquid. The liquid was stirred and mixed while maintaining the liquid temperature at about 20° C. to obtain aqueous liquid B-1.

After cooling the resulting aqueous mixed liquid A-1 to 70° C., 6.95 kg of silica sol containing 30.4% by mass as $SiO_2$ was added. Next, 0.88 kg of hydrogen peroxide containing 30% by mass as $H_2O_2$ was added followed by stirring and mixing for 1 hour at 50° C. Next, aqueous liquid B-1 was added. 0.37 kg of ammonium metatungstenate containing 50.2% by mass as $WO_3$ was then added followed by further adding a liquid in which 1.41 kg of fumed silica was dispersed in 19.71 kg of water to obtain a raw material mixture. The step of preparing the raw material mixture was repeated 10 times to prepare a total of about 80 kg of raw material mixture in order to continuously carry out the dry powder preparing step and calcining step.

(Preparation of Dry Powder)

A dry powder was obtained by carrying out spray drying in the same manner as Example 1.

(Classification Procedure)

Classification was carried out in the same manner as Example 1. The content of the dry powder particles having a particle diameter of 25 μm or less following classification was 2.1% by mass and the mean particle diameter was 55 μm.

(Calcination)

Calcination was carried out in the same manner as Example 1 to obtain an oxide catalyst. The reduction ratio of the catalyst precursor at this time was 10.16%.

(Evaluation of Catalyst Performance)

When the performance of the oxide catalyst in an ammoxidation reaction was evaluated in the same manner as Example 1, the propane conversion was 88.9% and the acrylonitrile yield was 52.8%.

Example 10

A catalyst represented by the compositional formula $Mo_1V_{0.24}Nb_{0.092}Sb_{0.26}B_{0.1}Ce_{0.006}O_n/44$ wt %-$SiO_2$ described below.

(Preparation of Raw Material Mixture)

3.62 kg of ammonium heptamolybdenate [$(NH_4)_6Mo_7O_{24}.4H_2O$], 0.57 kg of ammonium metavanadinate [$NH_4VO_3$], 0.77 kg of diantimony trioxide [$Sb_2O_3$], 0.054 kg of cerium nitrate [$Ce(NO_3)_3.6H_2O$] and 0.13 kg of boric acid [$H_3BO_3$] were add to 17.7 kg of water followed by heating for 2.5 hours at 90° C. while stirring to obtain aqueous mixed liquid A-1.

0.42 kg of hydrogen peroxide containing 30% by mass as $H_2O_2$ was added to 3.16 kg of the above-mentioned niobium raw material liquid. The liquid was stirred and mixed while maintaining the liquid temperature at about 20° C. to obtain aqueous liquid B-1.

After cooling the resulting aqueous mixed liquid A-1 to 70° C., 6.95 kg of silica sol containing 30.4% by mass as $SiO_2$ was added. Next, 0.90 kg of hydrogen peroxide containing 30% by mass as $H_2O_2$ was added followed by stirring and mixing for 1 hour at 50° C. Next, aqueous liquid B-1 was added. Moreover, a liquid in which 1.41 kg of fumed silica was dispersed in 19.7 kg of water was added to obtain a raw material mixture. Furthermore, the step of preparing the raw material mixture was repeated 10 times to prepare a total of about 80 kg of raw material mixture in order to continuously carry out the dry powder preparing step and calcining step.

(Preparation of Dry Powder)

A dry powder was obtained by carrying out spray drying in the same manner as Example 1.

(Classification Procedure)

Classification was carried out in the same manner as Example 1. The content of the dry powder particles having a particle diameter of 25 μm or less following classification was 1.6% by mass and the mean particle diameter was 53 μm.

(Calcination)

Calcination was carried out in the same manner as Example 1 to obtain an oxide catalyst. The reduction ratio of the catalyst precursor at this time was 9.5%.

(Evaluation of Catalyst Performance)

When the performance of the oxide catalyst in an ammoxidation reaction was evaluated in the same manner as Example 1, the propane conversion was 88.5% and the acrylonitrile yield was 52.6%.

Example 11

A catalyst represented by the compositional formula $Mo_1V_{0.22}Nb_{0.092}Sb_{0.25}W_{0.04}Mn_{0.003}O_n/44$ wt %-$SiO_2$ was produced in the manner described below.

(Preparation of Raw Material Mixture)

3.56 kg of ammonium heptamolybdenate [$(NH_4)_6Mo_7O_{24}\cdot 4H_2O$], 0.52 kg of ammonium metavanadinate [$NH_4VO_3$] and 0.76 kg of diantimony trioxide [$Sb_2O_3$] were added to 15.5 kg of water followed by heating for 2.5 hours at 90° C. while stirring to obtain aqueous mixed liquid A-1.

0.42 kg of hydrogen peroxide containing 30% by mass as $H_2O_2$ was added to 3.11 kg of the above-mentioned niobium raw material liquid. The liquid was stirred and mixed while maintaining the liquid temperature at about 20° C. to obtain aqueous liquid B-1.

After cooling the resulting aqueous mixed liquid A-1 to 70° C., 6.95 kg of silica sol containing 30.4% by mass as $SiO_2$ was added. Next, 0.89 kg of hydrogen peroxide containing 30% by mass as $H_2O_2$ was added followed by stirring and mixing for 1 hour at 50° C. Next, aqueous liquid B-1 was added. 0.017 kg of manganese nitrate [$Mn(NO_3)_2\cdot 6H_2O$] and 0.37 kg of ammonium metatungstenate containing 50% by mass as $WO_3$ were then added followed by further adding a liquid in which 1.41 kg of fumed silica was dispersed in 19.7 kg of water to obtain a raw material mixture. The step of preparing the raw material mixture was repeated 10 times to prepare a total of about 80 kg of raw material mixture in order to continuously carry out the dry powder preparing step and calcining step.

(Preparation of Dry Powder)

A dry powder was obtained by carrying out spray drying in the same manner as Example 1.

(Classification Procedure)

Classification was carried out in the same manner as Example 1. The content of dry powder particles having a particle diameter of 25 μm or less following classification was 1.9% by mass and the mean particle diameter was 54 μm.

(Calcination)

Clacination was carried out in the same manner as Example 1 to obtain an oxide catalyst. The reduction ratio of the catalyst precursor at this time was 10.25%.

(Evaluation of Catalyst Performance)

When the performance of the oxide catalyst in an ammoxidation reaction was evaluated in the same manner as Example 1, the propane conversion was 88.6% and the acrylonitrile yield was 52.9%.

Example 12

A catalyst represented by the compositional formula $Mo_1V_{0.24}Nb_{0.092}Sb_{0.26}Al_{0.009}O_n/44$ wt %-$SiO_2$ was produced in the manner described below.

(Preparation of Raw Material Mixture)

3.68 kg of ammonium heptamolybdenate [$(NH_4)_6Mo_7O_{24}\cdot 4H_2O$], 0.58 kg of ammonium metavanadinate [$NH_4VO_3$] and 0.79 kg of diantimony trioxide [$Sb_2O_3$] were added to 18.03 kg of water followed by heating for 2.5 hours at 90° C. while stirring to obtain aqueous mixed liquid A-1.

0.43 kg of hydrogen peroxide containing 30% by mass as $H_2O_2$ was added to 3.22 kg of the above-mentioned niobium raw material liquid. The liquid was stirred and mixed while maintaining the liquid temperature at about 20° C. to obtain aqueous liquid B-1.

After cooling the resulting aqueous mixed liquid A-1 to 70° C., 6.95 kg of silica sol containing 30.4% by mass as $SiO_2$ was added. Next, 0.92 kg of hydrogen peroxide containing 30% by mass as $H_2O_2$ was added followed by stirring and mixing for 1 hour at 50° C. Next, aqueous liquid B-1 was added. 0.0095 kg of aluminum oxide [$Al_2O_3$] was then added after dispersing in 0.29 kg of water followed by further adding a liquid in which 1.41 kg of fumed silica was dispersed in 19.71 kg of water to obtain a raw material mixture. The step of preparing the raw material mixture was repeated 10 times to prepare a total of about 80 kg of raw material mixture in order to continuously carry out the dry powder preparing step and calcining step.

(Preparation of Dry Powder)

A dry powder was obtained by carrying out spray drying in the same manner as Example 1.

(Classification Procedure)

Classification was carried out in the same manner as Example 1. The content of dry powder particles having a particle diameter of 25 μm or less following classification was 1.8% by mass and the mean particle diameter was 53 μm.

(Calcination)

Calcination was carried out in the same manner as Example 1 to obtain an oxide catalyst. The reduction ratio of the catalyst precursor at this time was 9.89%.

(Evaluation of Catalyst Performance)

When the performance of the oxide catalyst in an ammoxidation reaction was evaluated in the same manner as Example 1, the propane conversion was 87.7% and the acrylonitrile yield was 51.9%.

Example 13

A catalyst represented by the compositional formula $Mo_1V_{0.24}Nb_{0.092}Sb_{0.26}Ce_{0.005}Ta_{0.01}O_n/44$ wt %-$SiO_2$ was produced in the manner described below.

(Preparation of Raw Material Mixture)

3.64 kg of ammonium heptamolybdenate [$(NH_4)_6Mo_7O_{24}\cdot 4H_2O$], 0.58 kg of ammonium metavanadinate [$NH_4VO_3$], 0.78 kg of diantimony trioxide [$Sb_2O_3$], 0.045 kg of cerium nitrate [$Ce(NO_3)_3\cdot 6H_2O$] and 0.052 kg of tantalic acid were added to 17.2 kg of water followed by heating for 2.5 hours at 90° C. while stirring to obtain aqueous mixed liquid A-1.

0.43 kg of hydrogen peroxide containing 30% by mass as $H_2O_2$ was added to 3.18 kg of the above-mentioned niobium raw material liquid. The liquid was stirred and mixed while maintaining the liquid temperature at about 20° C. to obtain aqueous liquid B-1.

After cooling the resulting aqueous mixed liquid A-1 to 70° C., 6.95 kg of silica sol containing 30.4% by mass as $SiO_2$ was added. Next, 0.91 kg of hydrogen peroxide containing 30% by mass as $H_2O_2$ was added followed by stirring and mixing for 1 hour at 50° C. Next, aqueous liquid B-1 was added. Moreover, a liquid in which 1.41 kg of fumed silica were dispersed in 19.71 kg of water was added to obtain a raw material mixture. The step of preparing the raw material mixture was repeated 10 times to prepare a total of about 80 kg of raw material mixture in order to continuously carry out the dry powder preparing step and calcining step.

(Preparation of Dry Powder)

A dry powder was obtained by carrying out spray drying in the same manner as Example 1.

(Classification Procedure)

Classification was carried out in the same manner as Example 1. The content of dry powder particles having a particle diameter of 25 μm or less following classification was 2.0% by mass and the mean particle diameter was 52 μm.

(Calcination)

Calcination was carried out in the same manner as Example 1 to obtain an oxide catalyst. The reduction ratio of the catalyst precursor at this time was 9.95%.

(Evaluation of Catalyst Performance)

When the performance of the oxide catalyst in an ammoxidation reaction was evaluated in the same manner as Example 1, the propane conversion was 87.9% and the acrylonitrile yield was 52.1%.

Example 14

A catalyst represented by the compositional formula $Mo_1V_{0.24}Nb_{0.092}Sb_{0.26}O_n/47$ wt %-$SiO_2$ was produced in the manner described below.

(Preparation of Raw Material Mixture)

3.49 kg of ammonium heptamolybdenate [$(NH_4)_6Mo_7O_{24}\cdot 4H_2O$], 0.55 kg of ammonium metavanadinate [$NH_4VO_3$] and 0.75 kg of diantimony trioxide [$Sb_2O_3$] were added to 17.1 kg of water followed by heating for 2.5 hours at 90° C. while stirring to obtain aqueous mixed liquid A-1.

0.41 kg of hydrogen peroxide containing 30% by mass as $H_2O_2$ was added to 3.05 kg of the above-mentioned niobium raw material liquid. The liquid was stirred and mixed while maintaining the liquid temperature at about 20° C. to obtain aqueous liquid B-1.

After cooling the resulting aqueous mixed liquid A-1 to 70° C., 7.42 kg of silica sol containing 30.4% by mass as $SiO_2$ as added. Next, 0.87 kg of hydrogen peroxide containing 30% by mass as $H_2O_2$ was added followed by stirring and mixing for 1 hour at 50° C. Next, aqueous liquid B-1 was added. Moreover, a liquid in which 1.50 kg of fumed silica were dispersed in 21.1 kg of water was added to obtain a raw material mixture. Furthermore, the step of preparing the raw material mixture was repeated 10 times to prepare a total of about 80 kg of raw material mixture in order to continuously carry out the dry powder preparing step and calcining step.

(Preparation of Dry Powder)

A dry powder was obtained by carrying out spray drying in the same manner as Example 1.

(Classification Procedure)

Classification was carried out in the same manner as Example 1. The content of dry powder particles having a particle diameter of 25 μm or less following classification was 1.5% by mass and the mean particle diameter was 56 μm.

(Calcination)

Calcination was carried out in the same manner as Example 1 to obtain an oxide catalyst. The reduction ratio of the catalyst precursor at this time was 10.32%.

(Evaluation of Catalyst Performance)

When the performance of the oxide catalyst in an ammoxidation reaction was evaluated in the same manner as Example 1, the propane conversion was 89.0% and the acrylonitrile yield was 52.9%.

Example 15

A catalyst represented by the compositional formula $Mo_1V_{0.24}Nb_{0.092}Sb_{0.26}Ti_{0.008}O_n/44$ wt %-$SiO_2$ was produced in the manner described below.

(Preparation of Raw Material Mixture)

3.68 kg of ammonium heptamolybdenate [$(NH_4)_6Mo_7O_{24}\cdot 4H_2O$], 0.58 kg of ammonium metavanadinate [$NH_4VO_3$] and 0.79 kg of diantimony trioxide [$Sb_2O_3$] were added to 18.0 kg of water followed by heating for 2.5 hours at 90° C. while stirring to obtain aqueous mixed liquid A-1.

0.43 kg of hydrogen peroxide containing 30% by mass as $H_2O_2$ was added to 3.22 kg of the above-mentioned niobium raw material liquid. The liquid was stirred and mixed while maintaining the liquid temperature at about 20° C. to obtain aqueous liquid B-1.

After cooling the resulting aqueous mixed liquid A-1 to 70° C., 6.95 kg of silica sol containing 30.4% by mass as $SiO_2$ was added. Next, 0.92 kg of hydrogen peroxide containing 30% by mass as $H_2O_2$ was added followed by stirring and mixing for 1 hour at 50° C. Next, aqueous liquid B-1 was added. 0.013 kg of titanium oxide [$TiO_2$] stirred and dispersed in 0.14 kg of water was then added followed by further adding a liquid in which 1.41 kg of fumed silica were dispersed in 19.71 kg of water to obtain a raw material mixture. The step of preparing the raw material mixture was repeated 10 times to prepare a total of about 80 kg of raw material mixture in order to continuously carry out the dry powder preparing step and calcining step.

(Preparation of Dry Powder)

A dry powder was obtained by carrying out spray drying in the same manner as Example 1.

(Classification Procedure)

Classification was carried out in the same manner as Example 1. The content of dry powder particles having a particle diameter of 25 μm or less following classification was 2.1% by mass and the mean particle diameter was 51 μm.

(Calcination)

Calcination was carried out in the same manner as Example 1 to obtain an oxide catalyst. The reduction ratio of the catalyst precursor at this time was 9.99%.

(Evaluation of Catalyst Performance)

When the performance of the oxide catalyst in an ammoxidation reaction was evaluated in the same manner as Example 1, the propane conversion was 87.9% and the acrylonitrile yield was 51.8%.

Example 16

A catalyst represented by the compositional formula $Mo_1V_{0.24}Nb_{0.092}Te_{0.26}O_n/44$ wt %-$SiO_2$ was produced in the manner described below.

(Preparation of Raw Material Mixture)

3.74 kg of ammonium heptamolybdenate [$(NH_4)_6Mo_7O_{24}\cdot 4H_2O$], 0.59 kg of ammonium metavanadinate [$NH_4VO_3$] and 1.06 kg of telluric acid [$H_6TeO_6$] were added to 18.3 kg of water followed by heating for 2.5 hours at 90° C. while stirring to obtain aqueous mixed liquid A-1.

0.44 kg of hydrogen peroxide containing 30% by mass as $H_2O_2$ was added to 3.05 kg of the above-mentioned niobium raw material liquid. The liquid was stirred and mixed while maintaining the liquid temperature at about 20° C. to obtain aqueous liquid B-1.

After cooling the resulting aqueous mixed liquid A-1 to 70° C., 6.95 kg of silica sol containing 30.4% by mass as $SiO_2$ was added followed by stirring and mixing for 1 hour at 50° C. Next, aqueous liquid B-1 was added. Moreover, a liquid in which 1.41 kg of fumed silica was dispersed in 19.7 kg of water was added to obtain a raw material mixture. Furthermore, the step of preparing the raw material mixture was repeated 10 times to prepare a total of about 80 kg of raw material mixture in order to continuously carry out the dry powder preparing step and calcining step.

(Preparation of Dry Powder)

A dry powder was obtained by carrying out spray drying in the same manner as Example 1.

(Classification Procedure)

Classification was carried out in the same manner as Example 1. The content of dry powder particles having a particle diameter of 25 μm or less following classification was 2.2% by mass and the mean particle diameter was 50 μm.

(Calcination)

Calcination was carried out in the same manner as Example 1 to obtain an oxide catalyst. The reduction ratio of the catalyst precursor at this time was 9.7%.

(Evaluation of Catalyst Performance)

When the performance of the oxide catalyst in an ammoxidation reaction was evaluated in the same manner as Example 1, the propane conversion was 88.0% and the acrylonitrile yield was 52.4%.

The compositions of the oxide catalysts, physical properties, results of evaluating catalyst performance and the like are summarized in the following Tables 1 and 2. Furthermore, the fine content in the tables indicates the content of particles having a particle diameter of 25 μm or less (% by mass).

TABLE 1

|  | Composition | Other Conditions |
|---|---|---|
| Example 1 | $Mo_1V_{0.24}Nb_{0.092}Sb_{0.26}O_n$/44 wt %-$SiO_2$ |  |
| Example 2 | Same as above |  |
| Example 3 | Same as above |  |
| Example 4 | Same as above | Batch calcining |
| Example 5 | Same as above |  |
| Example 6 | Same as above |  |
| Example 7 | Same as above | Classification after pre-stage calcining |
| Comparative Example 1 | Same as above |  |
| Comparative Example 2 | Same as above |  |
| Comparative Example 3 | Same as above |  |
| Comparative Example 4 | Same as above |  |
| Comparative Example 5 | Same as above | Catalyst classification after main calcining |
| Comparative Example 6 | Same as above | Calcination in air |
| Example 8 | $Mo_1V_{0.24}Nb_{0.092}Sb_{0.26}W_{0.025}O_n$/44 wt %-$SiO_2$ |  |
| Example 9 | $Mo_1V_{0.24}Nb_{0.092}Sb_{0.26}W_{0.04}Ce_{0.008}O_n$/44 wt %-$SiO_2$ |  |
| Example 10 | $Mo_1V_{0.24}Nb_{0.092}Sb_{0.26}B_{0.1}Ce_{0.006}O_n$/44 wt %-$SiO_2$ |  |
| Example 11 | $Mo_1V_{0.22}Nb_{0.092}Sb_{0.25}W_{0.04}Mn_{0.003}O_n$/44 wt %-$SiO_2$ |  |
| Example 12 | $Mo_1V_{0.24}Nb_{0.092}Sb_{0.26}Al_{0.009}O_n$/44 wt %-$SiO_2$ |  |
| Example 13 | $Mo_1V_{0.24}Nb_{0.092}Sb_{0.26}Ce_{0.005}Ta_{0.01}O_n$/44 wt %-$SiO_2$ |  |
| Example 14 | $Mo_1V_{0.24}Nb_{0.092}Sb_{0.26}O_n$/47 wt %-$SiO_2$ |  |
| Example 15 | $Mo_1V_{0.24}Nb_{0.092}Sb_{0.26}Ti_{0.008}O_n$/44 wt %-$SiO_2$ |  |
| Example 16 | $Mo_1V_{0.24}Nb_{0.092}Te_{0.26}O_n$/44 wt %-$SiO_2$ |  |

TABLE 2

|  | Fine content (%) | Mean particle diameter (μm) | Overall reduction ratio (%) | Reduction ratio (%) >25 μm | Reduction ratio (%) ≤25 μm | Pn conversion (%) | AN yield (%) |
|---|---|---|---|---|---|---|---|
| Ex. 1 | 1.8 | 55 | 10.23 | — | — | 89 | 52.5 |
| Ex. 2 | 4.1 | 52 | 9.98 | — | — | 88.2 | 51.8 |
| Ex. 3 | 6.0 | 51 | 10.10 | — | — | 87.9 | 51.0 |
| Ex. 4 | 0.2 | 56 | 9.93 | — | — | 88.8 | 52.8 |
| Ex. 5 | 1.8 | 55 | 10.23 | — | — | 88.3 | 52.1 |
| Ex. 6 | 1.8 | 55 | 10.23 | — | — | 88.4 | 52.4 |
| Ex. 7 | 0.4 | 54 | 10.18 | — | — | 88.5 | 51.9 |
| Comp. Ex. 1 | 25.0 | 34 | 10.21 | 10.10 | 10.54 | 86 | 47.5 |
| Comp. Ex. 2 | 22.0 | 46 | 10.15 | 10.11 | 10.30 | 86.8 | 49.5 |
| Comp. Ex. 3 | 18.0 | 34 | 10.0 | 9.93 | 10.32 | 85 | 48.8 |
| Comp. Ex. 4 | 0.0 | 71 | 10.08 | — | — | 87.1 | 49.4 |
| Comp. Ex. 5 | 2.0 | 53 | 10.19 | — | — | 87.6 | 49.9 |
| Comp. Ex. 6 | 1.8 | 55 | 4.2 | 4.2 | 4.2 | 38.7 | 6.5 |
| Ex. 8 | 1.7 | 52 | 10.19 | — | — | 88.8 | 53 |
| Ex. 9 | 2.1 | 55 | 10.17 | — | — | 88.9 | 52.8 |
| Ex. 10 | 1.6 | 53 | 9.5 | — | — | 88.5 | 52.6 |
| Ex. 11 | 1.9 | 54 | 10.25 | — | — | 88.6 | 52.9 |
| Ex. 12 | 1.8 | 53 | 9.89 | — | — | 87.7 | 51.9 |
| Ex. 13 | 2.0 | 52 | 9.95 | — | — | 87.9 | 52.1 |
| Ex. 14 | 1.5 | 56 | 10.32 | — | — | 89 | 52.9 |
| Ex. 15 | 2.1 | 51 | 9.99 | — | — | 87.9 | 51.8 |
| Ex. 16 | 2.2 | 50 | 9.7 | — | — | 88 | 52.4 |

On the basis of the above results, an oxide catalyst obtained according to the production process of the present embodiment enabled the content of particles having a particle diameter of 25 μm or less and the mean particle diameter to be adjusted to within specified ranges, and demonstrated superior propane conversation rates and acrylonitrile yields in vapor-phase catalytic ammoxidation reaction of propane.

In contrast, in the case of the oxide catalysts of Comparative Examples 1 to 4, content of particles having a particle diameter of 25 μm or less and the mean particle diameter are unable to be adjusted to within specific ranges, and the propane conversion and acrylonitrile yields were inferior.

In addition, in the case of Comparative Example 5, the oxide catalyst was classified following main calcination, and the propane conversion and acrylonitrile yield were inferior.

Moreover, in the case of Comparative Example 6, calcination was carried out in air, and the propane conversion and acrylonitrile yield were inferior.

Thus, according to the present embodiment, a process was demonstrated to be able to be provided for producing an oxide catalyst for use in a vapor-phase catalytic oxidation or vapor-phase catalytic ammoxidation reaction of propane or isobutane that enables a catalyst demonstrating favorable yield to be produced both efficiently and stably.

The present application is based on a Japanese Patent Application (Japanese Patent Application No. 2007-333655) filed with the Japanese Patent Office on Dec. 26, 2007, the content of which is incorporated herein by reference.

INDUSTRIAL APPLICABILITY

According to the present invention, a process for producing an oxide catalyst used in a vapor-phase catalytic oxidation or vapor-phase catalytic ammoxidation reaction of propane or isobutane can be provided that enables a catalyst demonstrating favorable yield to be stably produced.

We claim:

1. A process for producing an oxide catalyst used in a vapor-phase catalytic oxidation or vapor-phase catalytic ammoxidation reaction of propane or isobutane, comprising the steps of:
   (i) preparing a catalyst raw material mixture containing Mo, V and Nb and satisfying the relationships of $0.1 \leq a \leq 1$ and $0.01 \leq b \leq 1$ when atomic ratios of V and Nb to one atom of Mo are defined as a and b, respectively,
   (ii) spray drying the raw material mixture to obtain catalyst precursor particles,
   (iii) classifying the catalyst precursor particles having a mean particle diameter of from 45 to 65 μm in which a content of the precursor particles having a particle diameter of 25 μm or less is 8% by mass or less, and
   (iv) pre-stage calcining the classified catalyst precursor particles in an inert gas atmosphere, wherein the pre-stage calcining is carried out continuously at a temperature from 250 to 400° C., to produce pre-stage calcined catalyst precursor particles having a reduction ratio of 8-12%,
   (v) main calcining the pre-stage calcined catalyst precursor particles in an inert gas atmosphere, wherein the main calcining is carried out continuously at a temperature from 550 to 800° C.

2. The process for producing the oxide catalyst according to claim 1, wherein the step (ii) is a step of spray drying the catalyst raw material mixture.

3. The process for producing the oxide catalyst according to claim 1, wherein a recovery rate of the particle in the classifying step is 75% by mass or more.

4. The process for producing the oxide catalyst according to claim 1, wherein the oxide catalyst is supported onto 10 to 80% by mass of silica in terms of $SiO_2$, based on a total weight of oxides of constituent elements of the catalyst and the silica.

5. The process for producing the oxide catalyst according to claim 1, wherein the step (iii) comprises a performing step of main calcining of pre-stage calcined catalyst precursor particles.

6. The process for producing the oxide catalyst according to claim 5, wherein a temperature range of the main calcination is from 550 to 800° C.

7. The process for producing the oxide catalyst according to claim 5, wherein a temperature range of the pre-stage calcination is from 250 to 400° C. and the temperature range of the main calcination is from 580 to 750° C.

8. The process for producing the oxide catalyst according to claim 5, wherein the calcination is carried out while rotating a calcining device.

9. A process for producing an unsaturated acid or an unsaturated nitrile, comprising the step of:
   bringing popane or isobutane into contact with an oxide catalyst obtained by the process according to claim 1, so as to carry out a vapor-phase catalytic oxidation or vaper-phase catalytic ammoxidation reaction.

* * * * *